United States Patent [19]

Laitinen

[11] Patent Number: 4,617,925
[45] Date of Patent: Oct. 21, 1986

[54] ADAPTER FOR DEFINITION OF THE POSITION OF BRAIN STRUCTURES

[76] Inventor: Lauri V. Laitinen, Nydalavägen 59, S-902 34 Umeå, Sweden

[21] Appl. No.: 655,671

[22] Filed: Sep. 28, 1984

[51] Int. Cl.[4] .................................................. A61B 17/00
[52] U.S. Cl. ................................................. 128/303 B
[58] Field of Search .................. 40/303 B; 33/174 D; 128/303, 663, 174 D

[56] References Cited

U.S. PATENT DOCUMENTS

| | | | |
|---|---|---|---|
| 3,135,263 | 6/1964 | Connelley | 128/303 B |
| 3,508,552 | 4/1970 | Hainault | 128/303 B |
| 4,341,220 | 7/1982 | Perry | 128/303 B |
| 4,350,159 | 9/1982 | Gouda | 128/303 B |
| 4,463,758 | 8/1984 | Patil et al. | 128/303 B |

*Primary Examiner*—Gene Mancene
*Assistant Examiner*—Wenceslao J. Contreras
*Attorney, Agent, or Firm*—Beveridge, DeGrandi & Weilacher

[57] ABSTRACT

This invention relates to an adapter for definition of the position of brain structures on a patient's head by means of spatial coordinates in computerized tomography and NMR examination and transferring the coordinates to a stereotactic apparatus, said adapter including ear supports carried by a first arm and a further support for reproducible fixation of the adapter to the patient's head, with two side frame parts adapted to be fitted on either side of the patient's head.

The novelty of this invention is that the adapter includes a second arm extending angularly to said first arm and forming together with the first arm and a further, third arm a triangular side frame structure, the side frame parts on either side of the patient's head being interconnected by means of connecting means which carry the further support and a laterality indicator means consisting of an anterior laterality indicator and two posterior laterality indicators for definition of a reference plane through the midline of the adapter.

12 Claims, 7 Drawing Figures

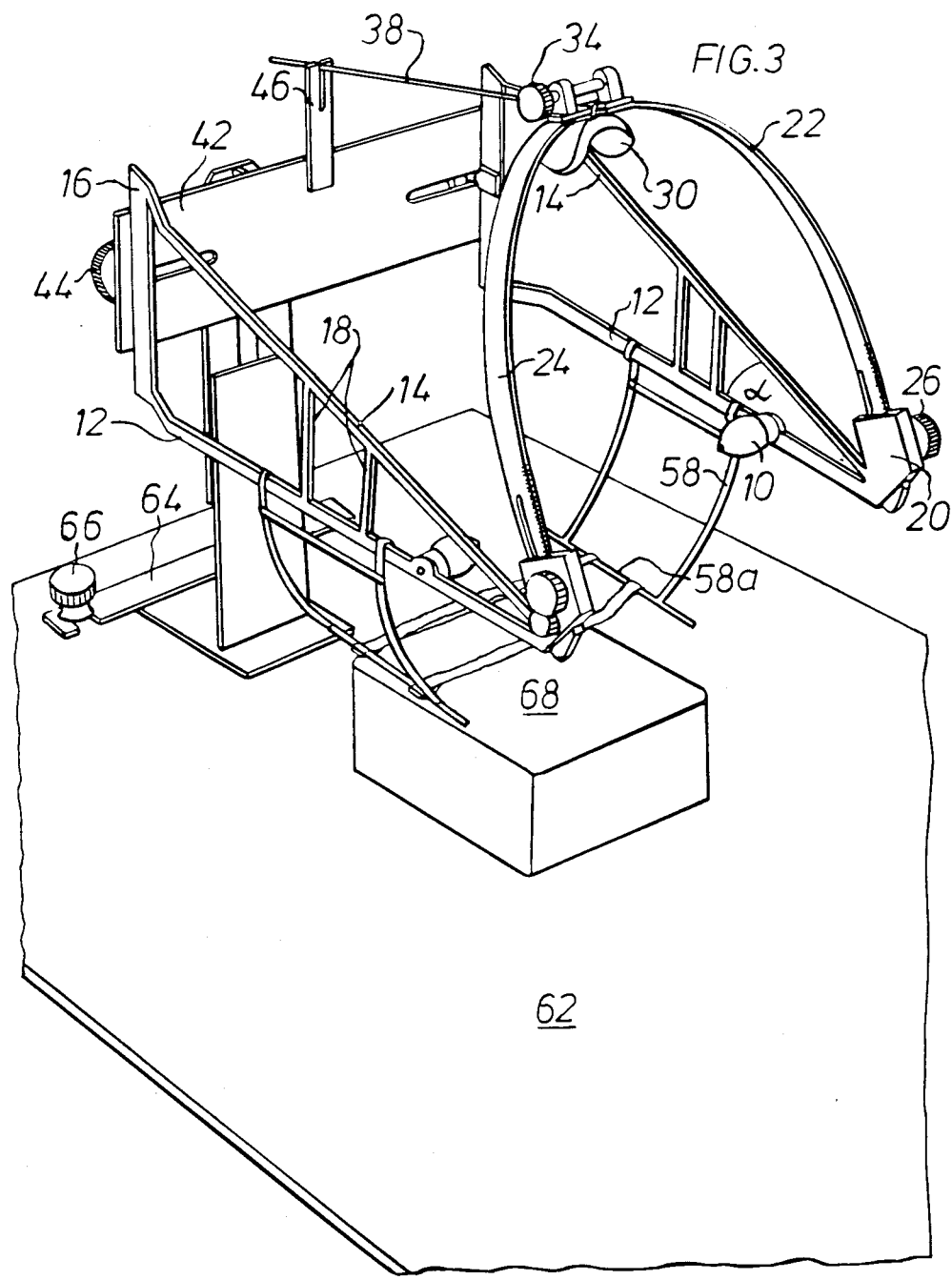

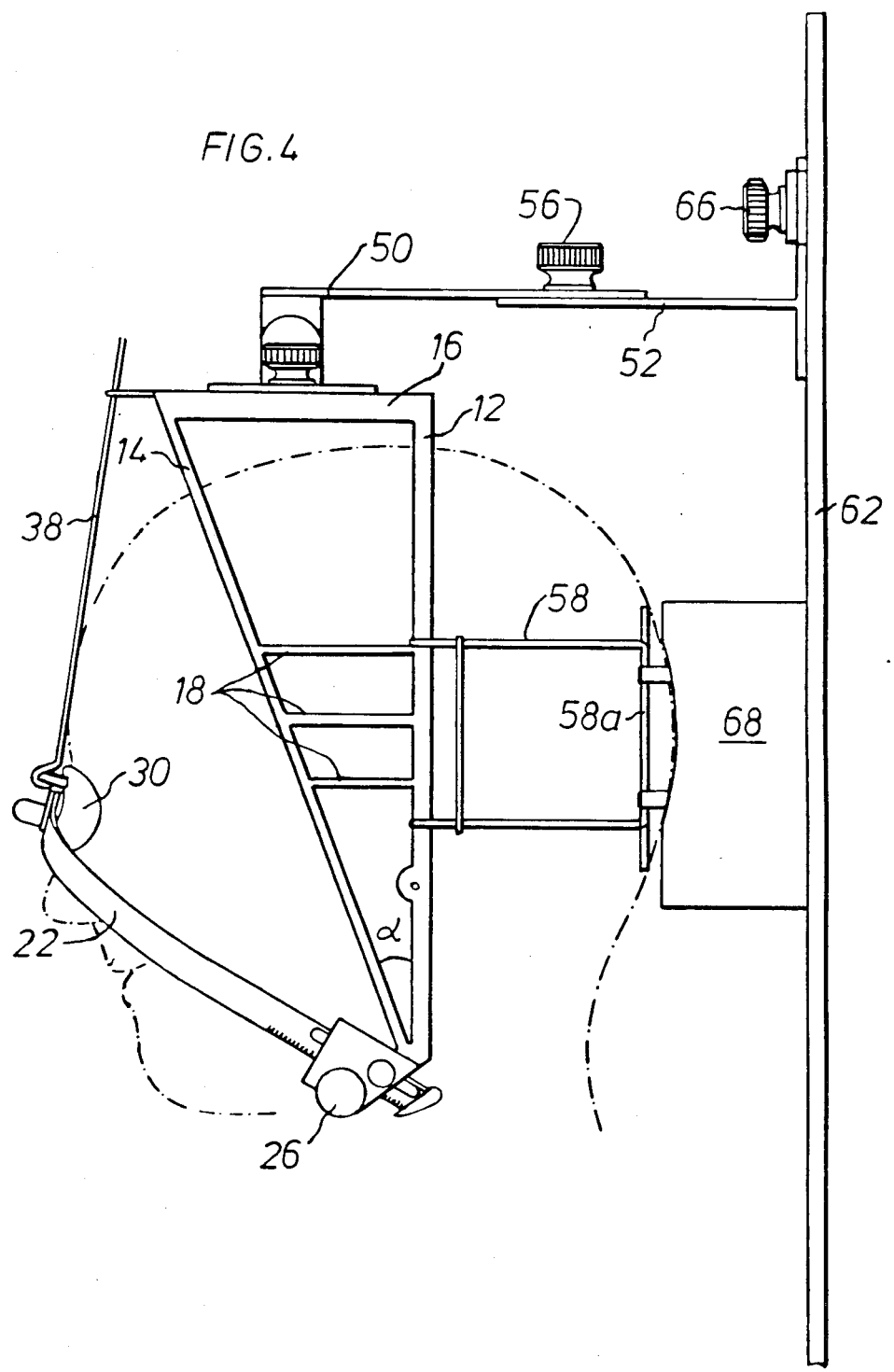

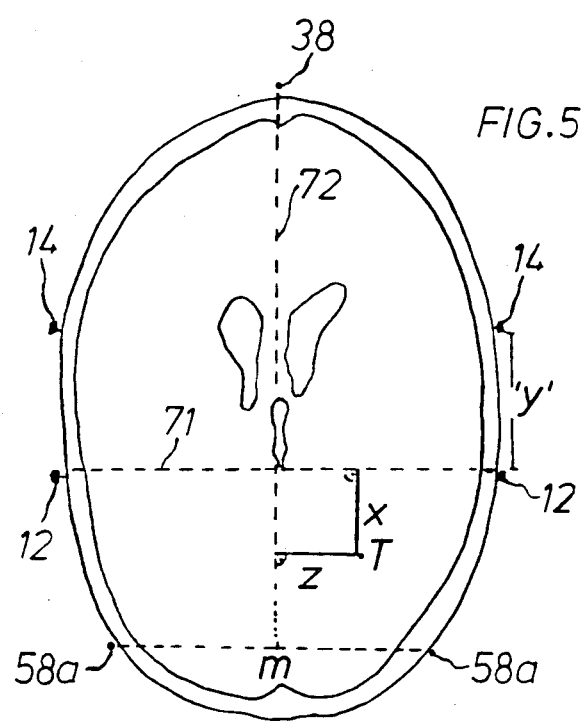

ADAPTER FOR DEFINITION OF THE POSITION OF BRAIN STRUCTURES

The present invention relates to an adapter as claimed in the preamble of claim 1 for definition of the position of brain structures by means of spatial coordinates in computerized tomography and NMR examination and transferring the coordinates to a stereotactic apparatus, said adapter including ear supports, nasion supports and laterality indicator systems for reproducible fixation of the adapter to the patient's head.

In examinations of and operations in a patient's head such as in computerized tomography examination and NMR examination (NMR means nuclear magnetic resonance) of the brain it is important that the position of brain structures can be defined by means of a reference system which can be reproducibly fixed repeatedly in the same position on the patient's head. This would permit studying during repeated examination whether or not these structures have changed shape or position, for instance due to tumor growth. It is also desirable that the computerized tomography coordinates can be transferred to a stereotactic apparatus so that surgical measures (thalamotomy, tumor treatment, implantation of electrodes, etc) can be carried out without any supplementary examinations, such as pneumoencephalography or angiography. Moreover, it is desirable stereotactically to irradiate, with the guidance of computerized tomography and NMR coordinates, deep brain structures with a conventional linear accelerator.

An ideal adapter for this purpose should fulfil the following criteria:

1. It should be non-invasive (not fixed to the skull with screws).
2. It should be relatively convenient to the patient, easy to fix and loosen.
3. It should permit being fixed to the head repeatedly in the same position.
4. It should permit accurate definition of brain coordinates in relation to the adapter.
5. It should permit being used with various types of stereotactic instruments.
6. One and the same adapter should permit use with all patients.

Several known attempts have been made to solve the above-mentioned problems and these attempts may be divided up into three main types. In the first case a computerized tomography study is performed with the patient fixed in a stereotactic apparatus. See U.S. Pat. Nos. 4,341,220 and 4,463,758. This method fulfils only criterium 4 of those enumerated above.

Another method in computerized tomography examinations is using bone reference points in the skull and then using the same reference points in the stereotactic operation. This method will thus require no equipment at all but it is inaccurate since it is rarely possible to find the same reference points in computer X-ray pictures and stereotactic X-ray pictures.

Still another method is fixing an adapter to the patient's head in a reproducible manner and one solution is based on a plastic mask which is cast on the patient's head, while a denture in the mouth aids in keeping the mask in proper position. This method fulfils criteria 1, 3 and 4 but is inconvenient to the patient, makes the stereotactic operation troublesome and does not at all fulfil criteria 5 and 6.

There are other known methods and apparatuses which are to fix the patient's head for X-ray examinations but these are not to take into consideration the position of brain structures. Examples of such methods and apparatuses are shown in SE Patent No. 131,423 and U.S. Pat. Nos. 2,532,967, 2,717,314, 2,846,587, 3,154,683, 3,514,606 and 4,256,112. None of the apparatuses shown in these patents permit, however, any accurate definition of brain coordinates in relation to the adapter and cannot be used together with stereotactic instruments.

The main object of the invention is to provide an adapter of the type described in the above introduction, making it possible to define the position of brain structures with the aid of a reference system which reproducibly can be fixed in the same position repeatedly on a patient's head. Another object is to define the position of the brain structures with the aid of three spatial coordinates in relation to desired reference structures so as to secure a three-dimensional definition of the position of these structures. Other objects are to provide an adapter fulfilling the above criteria 1-6, reducing the computerized tomography-NMR-examination time to a minimum and permitting using already existing stereotactic instruments in the neuro-surgical clinics in question. Another object is to provide an adapter which is inexpensive and easy to manufacture. Still another object is to make it possible to use the same adapter in external stereotactic irradiation of intra-cranial targets with a conventional linear accelerator and also in NMR-examination.

These and other objects of the invention are achieved in that the adapter has been given the characteristic features stated in the following claims.

The invention will be described in greater detail below with reference to the drawings, in which:

FIG. 3 shows how the adapter in FIG. 1 is fixed to the computerized tomography table;

FIG. 4 is a side view of the adapter fixed to the computerized tomography table after application to the patient's head;

FIG. 5 shows how the computerized tomography coordinates are defined on a computer picture;

Figure 1:
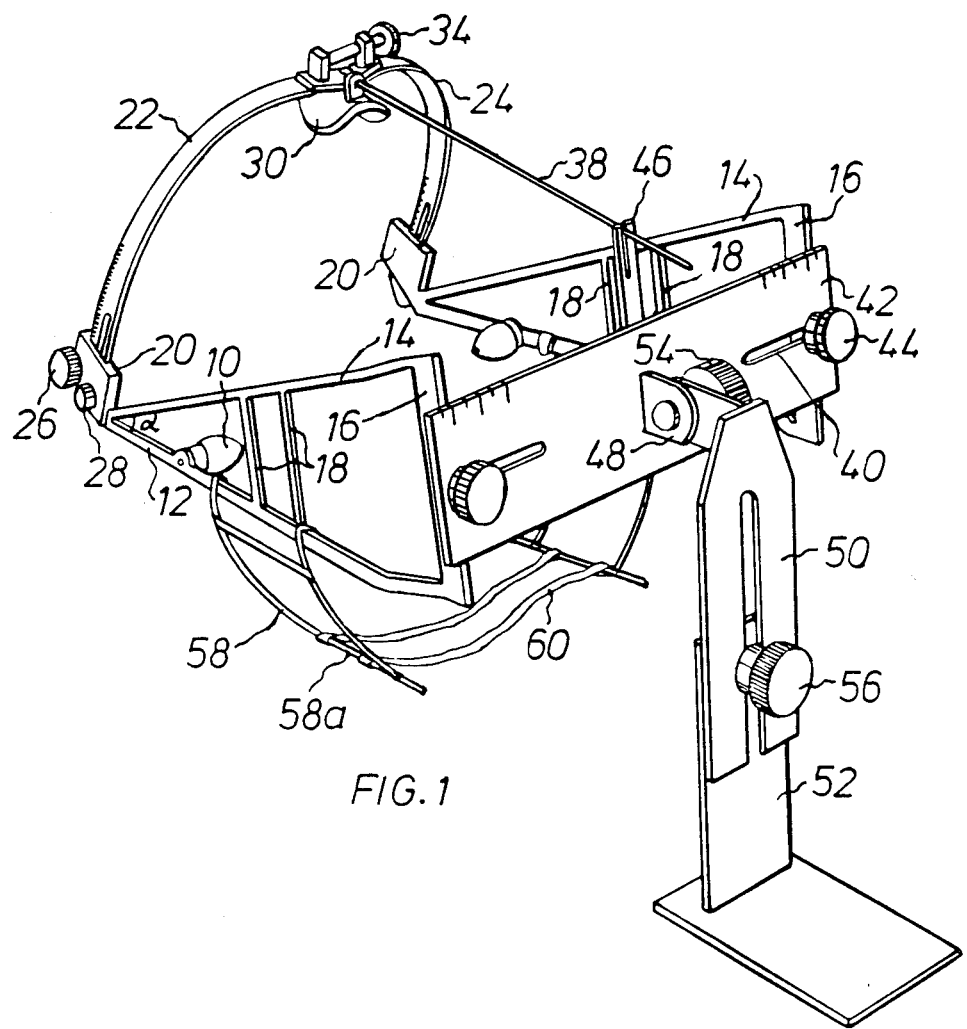
FIG. 1 is a perspective view of an adapter according to the invention.

The adapter shown in FIG. 1 includes a framework which is fixed to the patient's head by means of two ear supports and a nasion support. The components of the framework may be made of a suitable, somewhat springy material, such as plastics or light metal, preferably a hard aluminium alloy which is elastic but also other materials are of course conceivable. The almond-shaped ear supports 10 are fastened to that arm 12 which is posterior relative to the patient's face (FIG. 4) in a triangular frame part which also includes an anterior arm 14 and one or more arms 16 which connect the posterior 12 and anterior 14 arms. The ear supports 10 are preferably provided with air holes for pressure relief of the ear and for communication with the patient. The triangular frame part 12, 14, 16 has in the embodiment shown the shape of a right-angled triangle where the posterior arm 12 and the arm 16 constitute the smaller sides while the anterior arm 14 is the hypotenuse. The angle α between the arms 12 and 14 is acute and a preferred size of the angle is in the range of 10–30°, preferably 20°. In addition to the arm 16 which joins the posterior 12 and anterior 14 ear support arms and is perpendicular to the posterior 12 ear support arm there are arranged one or more transverse arms 18 which likewise extend perpendicularly to the posterior 12 ear support arm and join the arms 12, 14, all at a predetermined known distance from the ear supports.

Figure 2A:
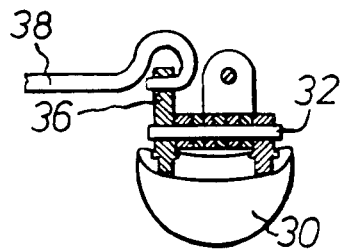
FIG. 2a is a section through the bearing of the nasion support on line II—II in FIG. 2b.
Figure 2B:
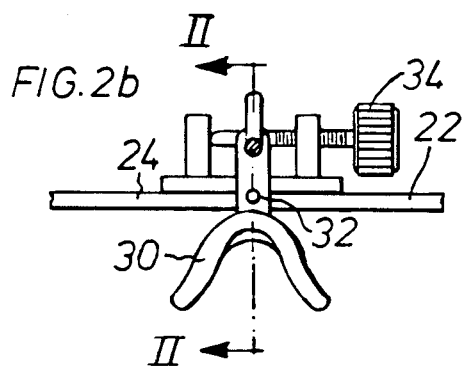
FIG. 2b is a frontal view of the nasion support.
Figure 2C:
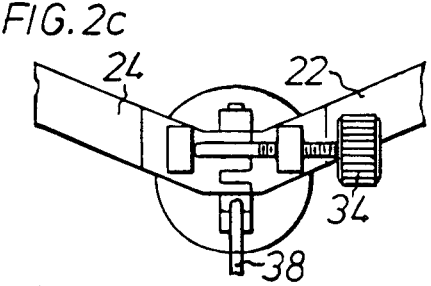
FIG. 2c is a plan view of the support of FIGS. 2a and 2b.

Fixed to the pointed end of the frame part 12–16 is a bearing bracket 20 through which the split end of two nasion support arms 22, 24 passes. The ends of these arms 22, 24 are in the form of racks meshing with a cogwheel which is borne in the bearing bracket 20 and can be operated from the outside by means of a wheel 26. The position of the arms 22 and 24 respectively set by means of the wheel 26 can be locked by means of a locking wheel 28. The end of the arms 22, 24 borne in the bearing bracket 20 is also provided with a scale, e.g. a millimetre scale for reproducible adjustment of the arms. The nasion support 30 which, as mentioned, is made of plastic or aluminium is of such a shape that it will rest with a wide surface against the upper part of the nasion. As is apparent from FIGS. 2a–2c the nasion support 30 is secured in the nasion support arms 22, 24 by means of a joint, such as a pin 32. With the aid of an adjusting screw 34 above the joint 32 the arms 22, 24 may be brought together while the ear supports 10 are at the same time pressed into the auditory meati as the screw 34 is tightened. As the screw is tightened 34 the arms 22, 24, which are borne in one another by means of the joint 32 and their labyrinth-shaped ends (FIG. 2c) will be pressed downwards together with the nasion support 30, as shown at the top of FIG. 1. The nasion support arms are made of an springy, shape-permanent material, and these arrangements therefore permit finding a pressure and a position of the nasion support 30 and the ear supports 10 which are steady but still tolerable to the patient. On the upper side of the nasion support 30 in the centre of the hinge of the joint 32 there is, as shown in FIG. 2a, an apertured attachment 36 for the frontal laterality indicator 38 which is in the form of a rod the bent or straight end of which engages in the attachment 36. The function of this rod 38 will be described in greater detail below.

Fixed in the middle of the arm 16 in the triangular frame parts is a threaded pin with a rectangular base part which is adjusted to a longitudinal slit 40 in a connector plate 42. In this way the triangular frame parts can be adjusted along the slit 40 and the set position is locked by means of a nut 44 in the form of a wheel, the set position being fixed so that the triangular frame parts 12, 14 will lie substantially perpendicularly to the connector plate and/or in contact with the patient's scalp. For indication of the set position the connector plate 42 is provided with a scale by means of which the setting of the triangular frame parts can be read. On the upper edge of the connector plate 42, as seen in FIG. 1, there is arranged a slit arm 46 in the slit of which the rod 38 is engaged and fixed. The connector plate 42 has also an attachment 48 which is fixed by means of a locking screw 54 to an angle bracket 50 which, in turn, is adjustable by means of a slit, and a wheel 56 engages with another angle bracket 52 in order to permit locking the adapter to a rectangular plate on the computerized tomography table, as will be described in greater detail below.

For the posterior laterality indication there is a system of posterior laterality indicators consisting of two symmetrical rectangular systems of metal wires 58 the ends of which are bent and can be fixed on a predetermined, marked point on the posterior ear support arms 12. In the posterior part of the system is an aluminium pin on either side as a posterior laterality indicator 58a. When the left-hand and the right-hand indicators 58 are joined with a rubber band 60 behind the back of the patient's head the aluminum pins will be pressed against the scalp (FIG. 1, 3, 4). The adapter is also suitable for definition of a position of brain structures for NMR examination when the arms 12 and 18 of the adapter and the laterality indicators 38 and 58a consist of plastic tubes filled with $H^{\pm}$ containing liquid.

As is apparent from FIGS. 3 and 4 the adapter is inserted on a plate 62 on the computerized tomography table by means of the angle bracket 52. The angle bracket is inserted in a clamp arm 64 with locking wheel 66. For fixation of the patient's head on the computerized tomography table there is arranged an rectangular plate 62, preferably of plastic or plexi glass, which has a cube-shaped raised portion, e.g. of plastics, which has a concave depression where the back of the patient's head will rest comfortably. The adapter shown in FIG. 1 is thus fixed with the patient's head to the plate 62 on the computerized tomography table (FIG. 4) with a system permitting stable immobilization. The intention is not to have the same position relative to the table during repeated examinations but rather to keep the head immobilized during the examination.

The adapter described above is fixed to the patient's head in the following way (FIGS. 1–4). The adjustment screw 34 of the nasion support 30 should be untightened, the nasion support arms 22, 24 be in their outermost position in the bearing brackets 20 and the connector plate 42 should be loosely fixed to the arms 16 of the triangular frame parts, while the almond-shaped ear supports 10 are pressed into the auditory meati, first on one side and then on the other side of the head. Once the two ear supports 10 are inside, the adjustment screw 34 at the nasion support 30 is tightened so that the ear supports will be kept steady in the interior of the meati. After that the nasion support 30 is pressed against the patient's nose bridge as the cogwheels 26 on both sides are turned at the same time. After the adjustment screw 34 has been further tightened and the cogwheels also have been tightened, the latter are locked with the locking screws 28. Then the triangle-shaped frame parts are adjusted until the connector plate 42 will lie symmetric relative to the arms 16 of the frame parts and perpendicular thereto or so that these arms will on both sides lie close to the scalp. Now the adapter lies in a reproducible position on the concerned patient's head and the adjustment value of all the four scales, i.e. at the two nasion support arms 22, 24 and at the ends of the connector plate 42 is recorded. The posterior laterality indicators 58 are clamped symmetrically at a suitable level to the posterior ear support arms 12. Then the anterior indicator or rod 38 is fixed between the nasion support 36 and the slit in the attachment 46. During repeated fixations of the adapter the anterior and the posterior laterality indicators will thus always lie in the same reproducible position at the scalp. These indicator systems further increase the stability of the adapter and are used to indicate the midline of the adapter in the patient's head to which the z-coordinates can be related both during the computerized tomography examination and the operation.

The patient now lies down on the plate 62 with the back of the head in the depression of the cube 68 and the head is turned so that the computer can make a tomography slice in parallel with the transverse arms 18 and thus at right angles to the posterior ear support arms 12. The adapter is now fixed rigidly to the table by means of the brackets 50, 52 and 64.

The computer coordinates and the NMR coordinates for the desired target T are measured in the following way, as will be described with reference to FIG. 5 which schematically shows a slice through the patient's head in parallel with the transverse arms 18 in FIG. 4. The distance between the shadows of the anterior 14 and posterior 12 ear support arms indirectly indicate the y-coordinate which is best referred to the level of the transverse arms 18. The latter are also used for checking, i.e. on those slices which are on level with the transverse arms 18 the whole arm should be visible. If they are visible at different levels on the left-hand or right-hand side the difference should be taken into consideration in determining the y-coordinate for structures lying at a varying distance from the midline. Several transverse arms involve that it is always possible to relate the slice level to an adjacent arm, which increases the exactitude for determination the y-coordinate.

As x-coordinate functions the distance of the target T from the line (71) joining the frontal edges of the posterior 12 ear support arm shadows (binaural plane). As z-coordinate there is indicated the distance of the target T from the midline (72) resulting when the shadow of the anterior laterality indicator or rod 38 is connected with the midpoint m on the line joining the shadows of the right-hand and the left-hand posterior laterality indicator 58a.

Figure 6:
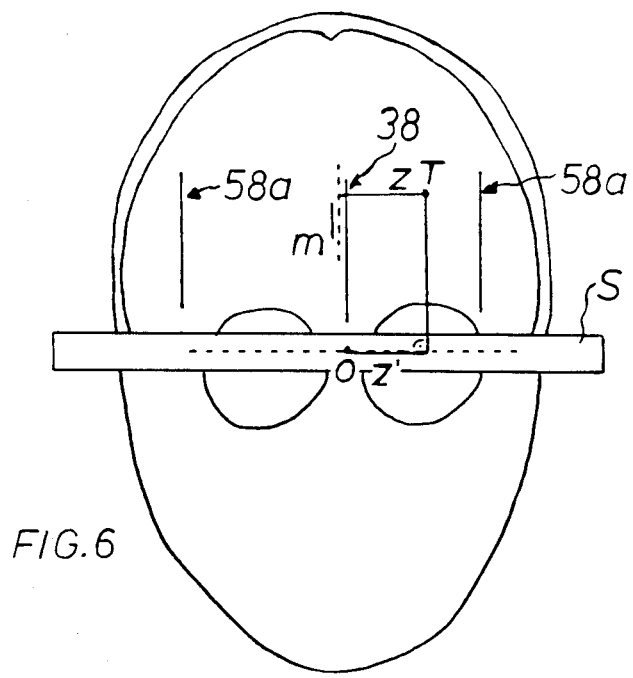
FIG. 6 is a schematic frontal view of the patient's head showing how the computerized tomography coordinates are transferred to stereotactic X-ray pictures.
Figure 7:
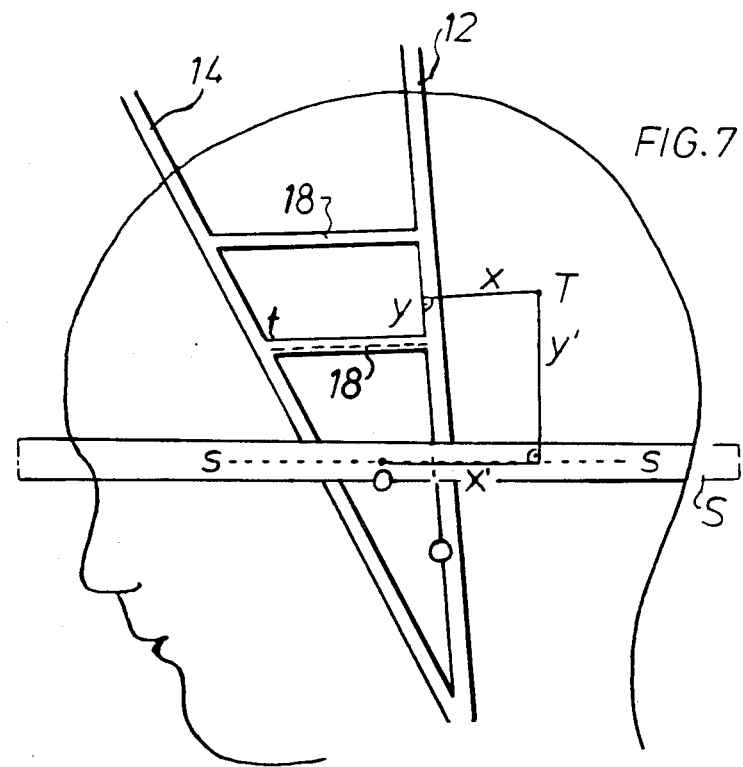
FIG. 7 is a schematic side view corresponding to the frontal view of FIG. 6.

When the computerized tomography coordinates are transferred to a stereotactic apparatus, which is schematically indicated at S in FIGS. 6 and 7, the adapter is fixed to the head as has been described above and with the same reading on the four scales as during the previous computerized tomography examination. The posterior laterality indicators 58 should also be fixed at the same level at the posterior ear support arms 12 as during the computerized tomography examination. After that the stereotactic apparatus is fixed to the patient's head, which is effected by screw insertion. On the frontal (antero-posterior) X-ray picture (FIG. 6) the shadows of respectively the anterior 38 and the posterior 58a laterality indicators are visualized, and the laterality of the computer target relative to the midline (72) of the adapter can thus be drawn in and be projected on the z-axis shadow of the stereotactic apparatus (s). On the lateral X-ray picture (FIG. 7) the shadows of the transverse (18) and the anterior (14) and posterior ear support arms 12 are visualized, and the binaural plane (71) b—b and the y-coordinate reference plane (transverse arm plane t) can then be drawn in. Thereupon the computer target T is drawn in according to the x- and y-coordinates and is projected on the x-axis shadow s-s of the stereotactic apparatus (s). In this connection we should not go into details regarding the influence of the magnification and direction of irradiation of the X-ray picture upon the purely stereotactic coordinate measurings.

As appears from the above, the adapter according to the invention permits obtaining a reference system which can be reproducibly fixed in the same position to the patient's head for computerized tomography-and NMP-examinations of the brain at the same time as the same reference system can be used to transfer, by means of a stereotactic apparatus fixed to the patient's head, the computer coordinates to stereotactic X-ray pictures, whereby the desired target in the brain can be reached with great accuracy. As is apparent, this takes place by means of three spatial coordinates x, y and z in relation to determined reference structures. The adapter also fulfils all the criteria which were stated in the introduction as desirable for such an apparatus. For the satisfactory function of the adapter in connection with a stereotactic operation it is also important that the adapter will take up a minimum of space inside the stereotactic apparatus. It is apparent that the present subject matter of patent also in this respect is planned with the utmost precision.

What I claim and desire to secure by Letters Patent is:

1. Adapter for definition of the position of brain structures on a patient's head by means of spatial coordinates in computerized tomography and NMR examination and transferring the coordinates to a stereotactic apparatus, said adapter including ear supports (10) carried by a first arm (12) and a further support (30) for reproducible fixation of the adapter to the patient's head, with two side frame parts adapted to be fitted on either side of the patient's head, wherein the adapter includes a second arm (14) extending angularly to said first arm (12) and forming together with the first arm (12) and a further, third arm (16) a triangular side frame structure (12, 14, 16), the side frame parts on either side of the patient's head being interconnected by means of connecting means (22, 24, 42) which carry the further support (30) and a laterality indicator means (38, 58a) consisting of an anterior laterality indicator (38) and two posterior laterality indicators (58a) for definition of a reference plane through the midline of the adapter.

2. Adapter as claimed in claim 1, wherein the further support (30) is a nasion support which is articulately connected with nasion support arms (22, 24) which, again, are adjustably connected with an end of the triangular side frame parts (12–16).

3. Adapter as claimed in claim 2, wherein the side frame parts (12, 14, 16) at their other end are adjustably connected by means of a connector plate (42).

4. Adapter as claimed in claim 2, wherein the nasion support arms (22, 24) are connected with the side frame parts (12, 14, 16) by means of bearings (20) arranged at said frame parts and in which racks on the nasion support arms (22, 24) engage with cogwheels (26) in the bearing means (20), said nasion support arms (22, 24) being lockable in the bearing brackets (20) and their position in the brackets being readable on a scale.

5. Adapter as claimed in claim 2, wherein the nasion support arms (22, 24) are connected by means of a bearing (32) which, by means of an adjustment screw (34), produces a leverage effect pressing the nasion support arms (22, 24), made of hard and somewhat springy material, and thus the side frame parts (12–16) against each other for pressing the ear supports (10) into the patient's auditory meati.

6. Adapter as claimed in claim 1, wherein the laterality indicator means includes an anterior, long laterality indicator (38) fixed between the nasion support (30) and an attachment (46) on the connector plate (42) and two posterior laterality indicators (58a) which are articulately arranged at the first arm (12) of the side frame parts and means (60) for pressing the posterior laterality indicators (58a) against the patient's head.

7. Adapter as claimed in claim 6, wherein the posterior laterality indicator are borne at the posterior arm (12) by means of arms (58) provided with hooks, and the means (60) for pressing the indicators against the patient's head consist of elastic bands which connect the posterior laterality indicators (58a).

8. Adapter as claimed in claim 1, wherein the adapter includes fastening means (48, 50, 52) for fixation to a computerized tomography table or the like.

9. Adapter as claimed in claim 1, wherein the side frame parts (12, 14, 16) are shaped as right-angled triangles in which the first arm (12) and the third arm (16) constitute the small sides while the second arm (14) constitutes the hypotenuse.

10. Adapter as claimed in claim 9, wherein one or more transverse arms (18) are arranged in parallel to the third arm (16) and lying at a known distance from the ear support (10).

11. Adapter as claimed in claim 9 wherein the acute angle in the triangle-shaped side frame parts (12, 14, 16) is between 10°–30°, preferably 20°.

12. Adapter as claimed in claim 1, wherein the anterior laterality indicator (38), the posterior laterality indicators (58a), the first arms (12) and the transverse arms (18) consist of tubes filled with liquid emitting a NMR-signal during NMR-examination.

* * * * *